(12) United States Patent
Bindra et al.

(10) Patent No.: US 12,254,447 B2
(45) Date of Patent: Mar. 18, 2025

(54) METHODS AND SYSTEMS FOR FINANCIAL MANAGEMENT AND RECONCILIATION WITHIN A DENTAL PROJECT MANAGEMENT SYSTEM

(71) Applicant: TechCo Holdings, Inc., Wilmington, DE (US)

(72) Inventors: Harmeetpal Singh Bindra, Gurgaon (IN); Niranjan Ramakrishnan, Tamil Nadu (IN)

(73) Assignee: TECHCO HOLDINGS, INC., Wilmington, DE (US)

( * ) Notice: Subject to any disclaimer, the term of this patent is extended or adjusted under 35 U.S.C. 154(b) by 95 days.

(21) Appl. No.: 18/189,832

(22) Filed: Mar. 24, 2023

(65) Prior Publication Data

US 2023/0306521 A1 Sep. 28, 2023

Related U.S. Application Data

(60) Provisional application No. 63/341,251, filed on May 12, 2022, provisional application No. 63/341,247, (Continued)

(30) Foreign Application Priority Data

Mar. 25, 2022 (IN) .............................. 202241017085
Mar. 25, 2022 (IN) .............................. 202241017090
Mar. 25, 2022 (IN) .............................. 202241017136

(51) Int. Cl.
*G06Q 10/10* (2023.01)
*A61B 5/00* (2006.01)
(Continued)

(52) U.S. Cl.
CPC ......... *G06Q 10/103* (2013.01); *A61B 5/0013* (2013.01); *G06Q 10/06395* (2013.01); (Continued)

(58) Field of Classification Search
CPC ........... G06Q 10/103; G06Q 10/06395; G06Q 10/087; G06Q 40/06; A61B 5/0013; G16H 20/10; G16H 30/20
See application file for complete search history.

(56) References Cited

U.S. PATENT DOCUMENTS

10,299,891 B2 5/2019 Lemchen et al.
10,548,691 B2 2/2020 Lemchen et al.
(Continued)

*Primary Examiner* — Scott S Trotter
(74) *Attorney, Agent, or Firm* — HSML P.C.

(57) ABSTRACT

Methods and systems for providing financial management and reconciliation within the dental project management system are provided. The method includes the dental project management system receiving an invoice associated with a particular dental product project. The method also includes an artificial intelligence (AI) validation module of the dental product management system automatically validating the invoice. Also, the method includes that upon validation of the invoice, the dental product management system requesting feedback from a doctor at a dental office. Further, the method includes the dental product management system receiving feedback from the doctor. Moreover, the method includes training the AI validation module based on the feedback from the doctor.

16 Claims, 4 Drawing Sheets

Related U.S. Application Data filed on May 12, 2022, provisional application No. 63/341,248, filed on May 12, 2022.

(51) Int. Cl.
| | | |
|---|---|---|
| *G06Q 10/0639* | (2023.01) | |
| *G06Q 10/087* | (2023.01) | |
| *G06Q 40/06* | (2012.01) | |
| *G16H 20/10* | (2018.01) | |
| *G16H 30/20* | (2018.01) | |

(52) U.S. Cl.
CPC .......... *G06Q 10/087* (2013.01); *G06Q 40/06* (2013.01); *G16H 20/10* (2018.01); *G16H 30/20* (2018.01)

(56) References Cited

U.S. PATENT DOCUMENTS

| | | |
|---|---|---|
| 11,284,969 B2 | 3/2022 | Lemchen et al. |
| 11,961,598 B1 * | 4/2024 | Finley ................... G06F 16/283 |

* cited by examiner

METHODS AND SYSTEMS FOR FINANCIAL MANAGEMENT AND RECONCILIATION WITHIN A DENTAL PROJECT MANAGEMENT SYSTEM

FIELD

This disclosure relates generally to dental management methods and systems between one or more dental offices, one or more dental labs, and one or more dental service organizations (DSOs). More specifically, this disclosure relates to methods and systems for providing financial management and reconciliation within a dental project management system.

BACKGROUND

Dental offices, dental laboratories and dental service organizations (DSOs) typically work together to prepare dental products for patients. These dental products can include, for example, crowns, bridges, dentures, dental implants, orthodontics, dental restorations, etc.

To order a dental product, one or more staff members at a dental office accesses an online web portal for the dental lab they want to prepare the product, fills out a dental product order form using the dental lab web portal, and attaches any additional information (e.g., a dental product prescription, X-rays, photos, etc.) that may be needed by the dental lab. When the dental lab receives the dental product order, a lab technician reviews the information, fabricates the dental product, and mails the dental product back to the dental office with an invoice for fabricating the dental product.

SUMMARY

This disclosure relates generally to dental management methods and systems between one or more dental offices, one or more dental labs, and one or more dental service organizations (DSOs). More specifically, this disclosure relates to methods and systems for providing financial management and reconciliation within a dental project management system.

In particular, the embodiments described herein can provide invoice management and digital payment reconciliation between one or more dental offices and one or more dental labs.

In some embodiments, a dental product management platform is provided that provides visibility from an initial patient visit at a dental office through a dental product project creation, a manufacturing lab invoice with dental product project sign off, and DSO payment reconciliation. The dental product management platform can include an artificial intelligence (AI) based module can speed up the invoice validation and authorization process by comparing the invoice with established business rules and previous user behavior based on AI training to validate the invoice. Accordingly, manual validation of invoices can be reduced. The embodiments described herein can provide automatic reconciliation where the AI module marks those invoices that pass without the need for manual intervention. In some embodiments, invoices in which the validation results are ambiguous can be pushed for manual reconciliation. The AI module can continue to learn from those projects that are sent for manual intervention in order to enhance its algorithm. A doctor at a dental office can receive an invoice for a dental product project with a dental product project sign off allowing the doctor to provide feedback through the dental product management platform on the quality of the work of the dental lab designing and/or fabricating the dental product. Thus, any invoice reconciliation performed by the AI module can be validated once more from the doctor which can then be added to the training of the AI module. Accordingly, the dental product management platform can assist DSOs in identifying and monitoring key focus areas.

The embodiments described herein can also provide an interactive voice response (IVRS) in sync with the dental product management platform and can identify a doctor/practice based on an incoming call number and can provide dental product project-specific and/or dental lab-specific information on a dental product project, shipment, invoice, billing status, etc.

In one embodiment, a method for providing financial management and reconciliation within the dental project management system is provided. The method includes the dental project management system receiving an invoice associated with a particular dental product project. The method also includes an AI validation module of the dental product management system automatically validating the invoice. Also, the method includes that upon validation of the invoice, the dental product management system requesting feedback from a doctor at a dental office. Further, the method includes the dental product management system receiving feedback from the doctor. Moreover, the method includes training the AI validation module based on the feedback from the doctor.

In another embodiment, a dental product management system configured to provide financial management and reconciliation is provided. The dental product management system includes an AI validation module configured to automatically validate an invoice associated with a particular dental product project. The dental project management system is configured to receive the invoice. Also, upon validation of the invoice, the dental product management system is configured to request feedback from a doctor at a dental office. Further, the dental product management system is configured to receive feedback from the doctor. The dental product management system is also configured to train the AI validation module based on the feedback from the doctor.

BRIEF DESCRIPTION OF THE DRAWINGS

References are made to the accompanying drawings that form a part of this disclosure, and which illustrate embodiments in which the systems and methods described in this Specification can be practiced.

Like reference numbers represent like parts throughout.

DETAILED DESCRIPTION

This disclosure relates generally to dental management methods and systems between one or more dental offices, one or more dental labs, and one or more dental service organizations (DSOs). More specifically, this disclosure relates to methods and systems for providing financial management and reconciliation within a dental project management system.

It is noted that: U.S. application Ser. No. 18/189,825, "METHODS AND SYSTEMS FOR BI-DIRECTIONAL INTEGRATION BETWEEN AN INTRAORAL SCANNER AND A DENTAL LAB,"; and U.S. application Ser. No. 18/189,828, "METHODS AND SYSTEMS FOR INTEGRATED DESIGN WORKFLOW BETWEEN AN INTRAORAL SCANNER, A DESIGN SERVICE AND A MILLING CENTER,"; all filed concurrently herewith on Mar. 24, 2023, and the contents of which are incorporated herein by reference.

Figure 1:
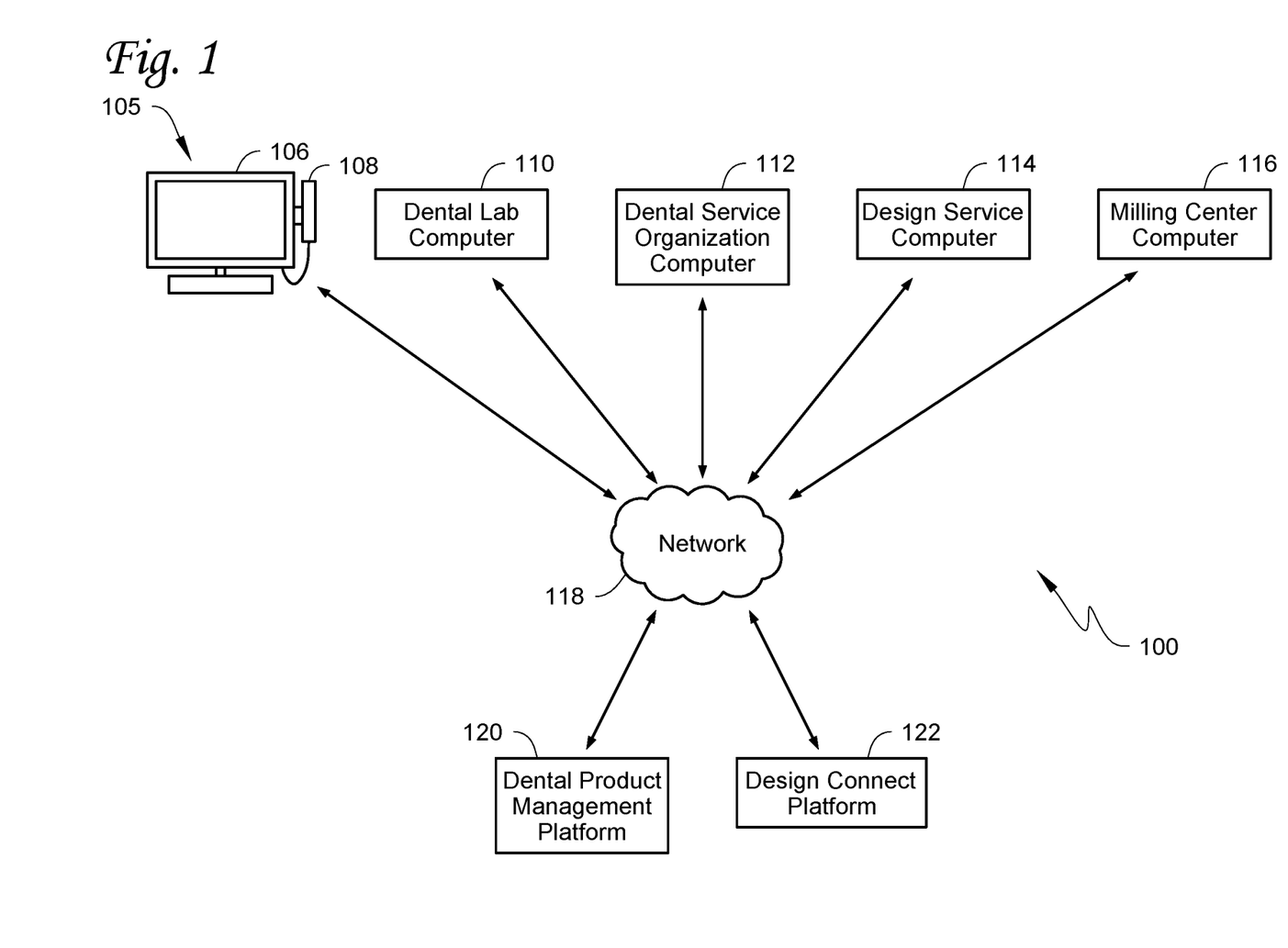
FIG. 1 illustrates a dental product management system, according to one embodiment.

FIG. 1 illustrates a dental product management system 100, according to one embodiment. The system 100 includes an intraoral scanner (IOS) 105 at a dental office, a dental lab computer 110 at a dental lab, a dental service organization (DSO) computer 112 at a DSO that are connected to a dental product management platform 120 via a network 118. The system 100 also includes a design service computer 114 and a milling center computer 116 connected to a design connect platform 122 via the network 118. The dental product management platform 120 is connected to the design connect platform 122 via the network 118. It will be appreciated that while only a single intraoral scanner, dental lab, DSO, design service and milling center are shown in FIG. 1, in other embodiments there may be multiple intraoral scanners, dental labs and/or DSOs connected to the dental product management platform 120 and there may be multiple design services and/or milling centers connected to the design connect platform 122.

The intraoral scanner 105 is an electronic device configured to obtain image data (e.g., 3D image data) of anatomical structures within the mouth of a patient. The image data can be used to create a dental product such as, for example, a crown, bridge, denture, dental implant, orthodontic, dental restoration, etc. The intraoral scanner 105 can be located at, for example, a dental office. The intraoral scanner 105 includes a computer 106 and a wand 108. An operator (e.g., dentist, dental hygienist, technician, etc.) at a dental office can use the wand 108 to scan a patient's mouth to obtain image data. The computer 106 can include one or more processors for both controlling operation of the wand 108, including coordinating the scanning and in reviewing and processing the scanning and generation of the image data including surface and internal features. The one or more processors may include or may be coupled with a memory for storing the scanned image data (surface data, internal feature data, etc.). The computer 106 can include one or more inputs (e.g., buttons, touchscreen, keyboard, etc.) to allow operator input for controlling scanning and operation of the intraoral scanner 105. Also, the computer 106 can include a display for allowing the operator to view the scanned image data and other information related to operation of the intraoral scanner 105. The computer 106 can also include communications circuitry, including wireless or wired communications circuitry, for communicating with the wand 108 and/or accessing the dental product management platform 120 via network 118. For example, the computer 106 may be configured to allow the operator to prepare a dental product prescription and combine scanned image data with the dental product prescription using the dental product management platform 120. The computer 106 can be the same as or similar to aspects of the computer device 500 as shown and described in accordance with FIG. 4 below.

The dental lab computer 110 is a computer at a dental lab that is configured to receive dental product prescriptions with scanned image data, fabricate a desired dental product as requested in the dental product prescription, and provide the fabricated dental product to the desired recipient (e.g., a dental office where the intraoral scanner 105 is located). In some embodiments, the dental lab computer 110 is at a location different from the location of the intraoral scanner 105. The dental lab computer 110 is configured to access the dental product management platform 120 via the network 118 to, for example, receive dental product prescriptions and scanned image data. The dental lab computer 110 can be the same as or similar to aspects of the computer device 500 as shown and described in accordance with FIG. 4 below.

The DSO computer 112 is a computer of a DSO that is configured to provide business management and support for one or more dental offices including a dental office where the intraoral scanner is located. In some embodiments, the DSO computer 112 is at a location different from the locations of the intraoral scanner 105 and the dental lab computer 110. The DSO computer 112 is configured to access the dental product management platform 120 via the network 118 to, for example, track dental product management status between one or more dental offices and one or more dental labs, verify and approve invoicing between one or more dental offices and one or more dental labs, obtain quality analysis of dental product orders, obtain dental product orders volume analysis, obtain purchase value analysis of the dental product orders, obtain turnaround time for dental product orders for the one or more dental labs, obtain benchmarking analysis of the dental product orders, etc. The DSO computer 112 can be the same as or similar to aspects of the computer device 500 as shown and described in accordance with FIG. 4 below.

Figure 2:
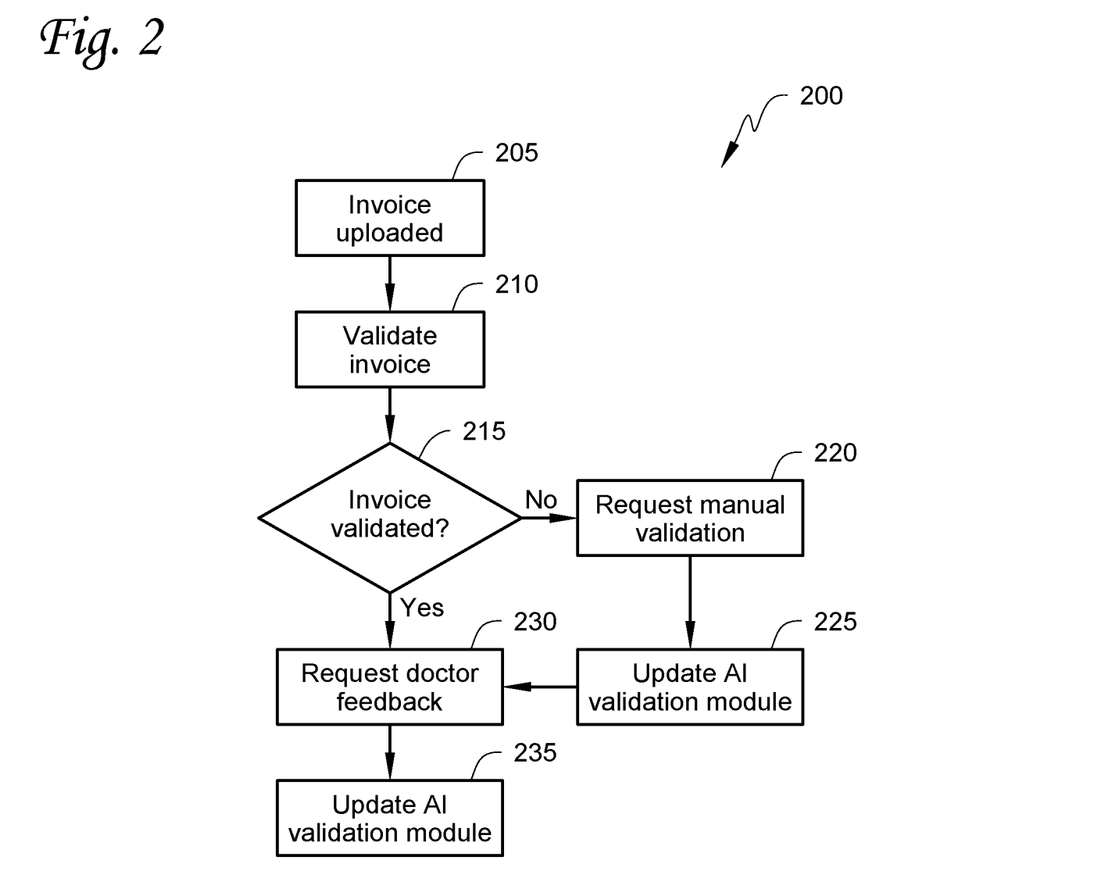
FIG. 2 illustrates a flowchart of a method for providing financial management and reconciliation within a dental project management system, according to one embodiment.
Figure 3:
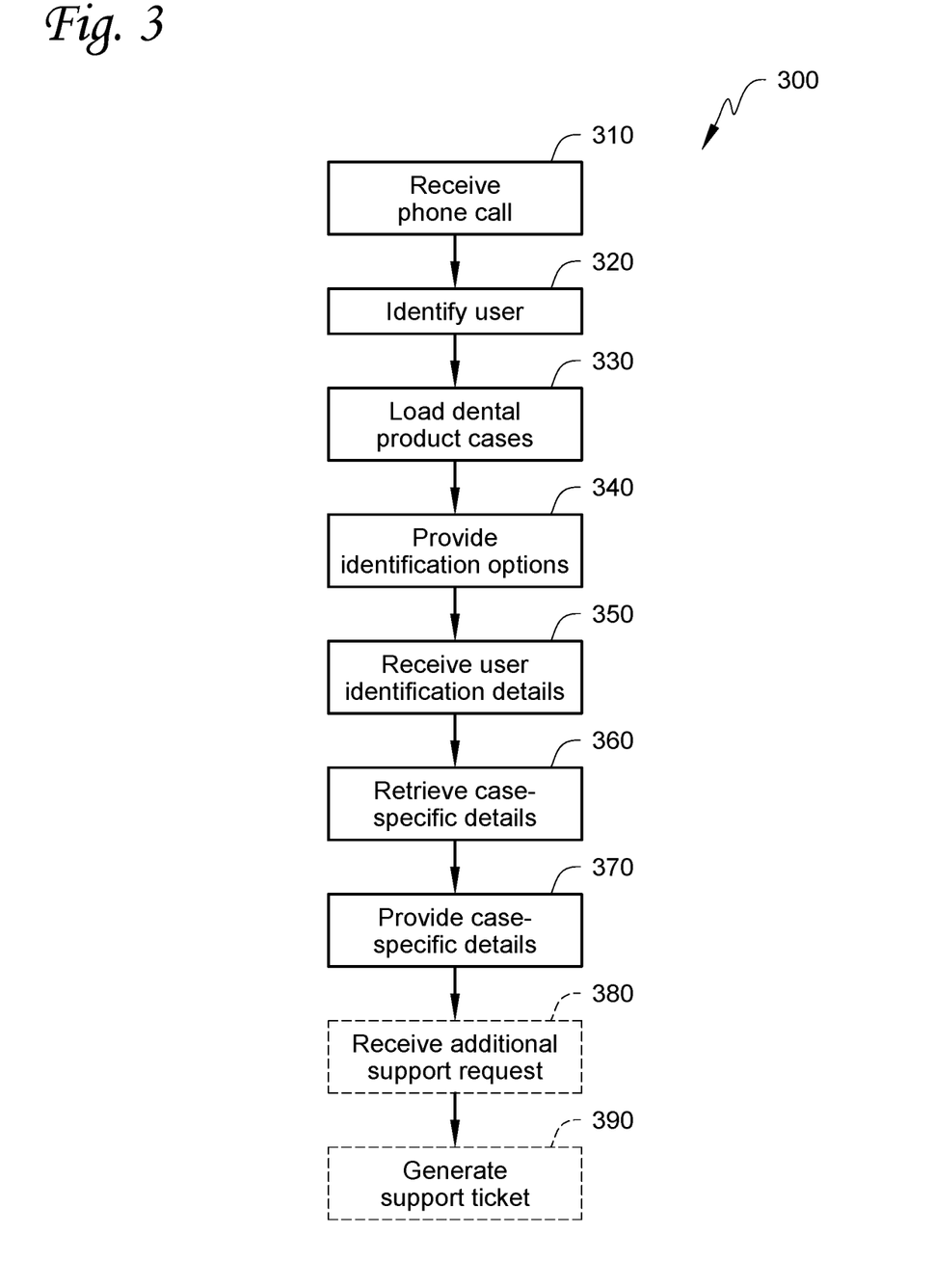
FIG. 3 illustrates a flowchart of a method for providing interactive voice response (IVRS) within the dental project management platform while a user is calling a support phone number of the dental product management system, according to one embodiment.

The dental product management platform 120 is configured to provide an online management platform that can connect one or more dental offices (e.g., via an intraoral scanner), one or more dental labs, and one or more DSOs. The intraoral scanner 105, the dental lab computer 110, and the DSO computer 112 can access the dental product management platform 120 via, for example, a graphical user interface (GUI) accessible via a website and/or online software application. The dental product management platform 120 can include one or more application programming interfaces (APIs) that enable, for example, bi-directional intraoral scanner integration between the intraoral scanner 105 and the dental lab computer 110 (as shown in FIG. 2 and described in more detail below); prescription standardization across digital and non-digitized dental product prescriptions across all participating dental offices and dental labs; financial reconciliation from an initial patient visit through a dental office dental product prescription creation, manufacturing lab invoice with dental product order sign off, and DSO payment reconciliation; and interactive voice response (IVRS) to provide order specific and lab specific information on a dental product order, shipment, invoice, billing statuses, etc. (as shown in FIG. 3 and described in more detail below); etc. In some embodiments, the dental product management platform 120 can be supported by one or more servers similar to the server device 535 shown and described in accordance with FIG. 4 below. The dental product management platform 120 is also configured to communicate with the design connect platform 122. In some embodiments, the dental product management platform 120 and the design connect platform 122 are part of the same platform. For example, in some embodiments the dental product management platform 120 can be connected to the design connect platform 122 via an interface layer. In some embodiments, the dental product management platform 120 can be a cloud based application platform.

The design service computer 114 is a computer configured to provide designer services to design a dental product. In some embodiments, the design service computer 114 is a computer of a design service that is configured to provide designer services for one or more dental offices including a dental office where the intraoral scanner is located. In some embodiments, the design service computer 114 is at a location different from the locations of the intraoral scanner 105 and the dental lab computer 110. In some embodiments, the design computer 114 can be located at a dental office where the intraoral scanner 105 is located. In some embodiments, the design computer 114 can be located at a design center where the dental lab computer 110 is located. In some embodiments, the design service computer 114 is at a location different from the locations of the intraoral scanner 105 and the dental lab computer 110. The design service computer 114 is configured to access the design connect platform 122 via the network 118 to, for example, obtain dental product order(s) with dental product prescription and scanned image data to allow a designer to generate a design of the desired dental product. The design service computer 114 can be the same as or similar to aspects of the computer device 500 as shown and described in accordance with FIG. 4 below.

The milling center computer 116 is a computer of a milling center that is configured to provide milling services for one or more dental offices including a dental office where the intraoral scanner is located. In some embodiments, the milling center computer 116 can be located where the design computer 114 is located. In some embodiments, the milling center computer 116 is at a location different from the locations of the intraoral scanner 105, the dental lab computer 110, and potentially the design service computer 114. The milling center computer 116 is configured to access the design connect platform 122 via the network 118 to, for example, obtain a generated design of the dental product to allow the milling service to fabricate the desired dental product. In some embodiments, the milling center computer 116 can be configured to access the design connect platform 122 via the network 118 to, for example, obtain dental product order(s) with a dental product prescription and scanned image data to allow a designer at the milling center to generate a design of the desired dental product and then allow the milling service to fabricate the desired dental product. In some embodiments, the milling center computer 116 can be configured to access the dental product management platform 120 via the network 118 to, for example, obtain dental product order(s) with a dental product prescription and scanned image data directly from, for example, the intraoral scanner 105 to allow a designer at the milling center to generate a design of the desired dental product and then allow the milling service to fabricate the desired dental product. The milling center computer 116 can be the same as or similar to aspects of the computer device 500 as shown and described in accordance with FIG. 4 below.

The design connect platform 122 is configured to provide an online design platform that can connect one or more dental labs, one or more design services and one or more milling services. The dental lab computer 110, the design service computer 114 and the milling center computer 116 can access the design connect platform 122 via, for example, a graphical user interface (GUI) accessible via a website and/or online software application. The design connect platform 122 can enable, for example, an integrated design workflow and manufacturing from the dental lab (via the dental lab computer 110) to the design service (via the design service computer 114) and to the milling center (via the milling center computer 116); tracking dental product order(s); real time turnaround time and quality analysis reports; etc. Accordingly, a design center having the design service computer 114 can use the design connect platform 122 to manage design services. In some embodiments, the dental product management platform 120 can be supported by one or more servers similar to the server device 535 shown and described in accordance with FIG. 4 below. The design connect platform 122 is also configured to communicate with the dental product management platform 120. In some embodiments, the design connect platform 122 can interact with the dental product management platform 120 to access dental product orders submitted by, for example, the intraoral scanner 105. In some embodiments, the dental product management platform 120 and the design connect platform 122 are part of the same platform. In some embodiments, the dental product management platform 120 can be a cloud based application platform.

In some embodiments, the design connect platform 122 can include a customer portal GUI, a designer portal GUI and an admin portal GUI. The customer portal GUI can be accessible via the dental lab computer 110. In some embodiments, the customer portal GUI is configured to provide a dashboard that can display live dental product orders, on hold dental product orders, in production dental product orders, completed dental product orders, turnaround time for completed dental product orders, etc. In some embodiments, a user, via the customer portal GUI, can upload a dental product prescription and/or scanned image data, select a turnaround time, a destination, a design software, a model requirement, a design approval requirement before placing the dental product order, etc. In some embodiments, the customer portal GUI can also display a dental product order list that includes dental product orders that are new, live on hold, in production, completed, cancelled, etc. In some embodiments, the customer portal GUI can support, for example, dental product order cancellation requests, dental product re-design requests, dental product quality concern requests, dental product billing/payment issue requests, customer portal GUI issue requests, file/attachment issue requests, etc. In some embodiments, the customer portal GUI can store and support user accounts and design preferences for a particular user profile. In some embodiments, the customer portal GUI can include options to make payment(s), access invoice(s), and review payment history. In some embodiments, the customer portal GUI can provide the user with production status on one or more dental product orders, a daily dental product order report and can provide a dental product order archive.

The designer portal GUI can be accessible via the design service computer 114. In some embodiments, the designer portal GUI is configured to provide a dashboard that can display dental product order design(s), dental product order validation(s), and dental product order draft(s). In some embodiments, the designer portal GUI can include: functionality for uploading IOS cases when, for example, the dental lab is automating dental product order creation from intraoral scanners including the intraoral scanner 105; functionality for opening multiple dental product orders; functionality for creating new dental product order(s); a timer for tracking time to complete a dental product order via the designer portal GUI; widgets for viewing current dental product order queue to take cation upon; and an order panel to view dental product order details being worked upon with links for checkout, return, hold, etc. A checkout link can signify activity completion for any user. For example, selection of a checkout link can indicate that the design is completed for a dental product case. In another example, selection of a checkout link can indicate that quality control of a design is completed for a dental product case. A return link can push a dental product case back to, for example, a shift supervisor, an admin user, a customer, etc. The return link can be selected, for example, when the user of the design connect platform 122 has a query, scanned image data is not clear, etc. A hold link can signify that a dental product case is to be put on hold, for example, when the dental product case is returned to a customer. In some embodiments, a returned dental product case can be put on hold if, for example, the dental product case is returned back to the customer. In some embodiments, only customer may have sufficient rights to restart or cancel a dental product case. In some embodiments, the designer portal GUI can be used to find a particular dental product order by, for example, a dental product order number, a dental product order name, a draft dental product order number, etc. In some embodiments, the designer portal GUI can access a dental product order and begin working on the dental product order. This can include the designer portal GUI being able to access and display dental product order details, files/attachments, design preferences, messages, instructions, etc.

The admin portal GUI can be accessible via design service computer 114. In some embodiments, the admin portal GUI is configured to provide a dashboard that can display dental product accounts, new dental product orders, dental product orders in progress, dental product order tasks, completed dental product orders, on hold dental product orders, re-work dental product orders, delayed dental product orders, cancelled dental product orders, rush dental product orders, dental product order feedback, signup requests for new customer registrations waiting to be approved to start using the design connect platform 122, etc. In some embodiments, the admin portal GUI can include dental product transactions, accounts receivables, reports, master data, user management, admin setup, etc. In some embodiments dental product transactions can include order correction (e.g., a utility for an admin to correct any details of a dental product order once submitted by a customer (e.g., design preferences, remarks, design model only, turnaround time, etc.), upload/download files/attachment(s) (e.g., a utility for an admin to upload a corrected file or any additional files for customer reference), support ticket(s) that can allow a customer to request support, shift allocation that can allow a supervisor to designer(s) to different shifts, re-design dental product order(s) that can allow a customer or an admin (based on a customer request) to request a re-design of a completed dental product order, restart previously closed or on hold dental product order(s) by a customer or an admin (based on a customer request), etc. In some embodiments, the accounts receivables can include sales invoice(s), customer receipt(s), open invoice(s), accounts receivable report(s), etc. In some embodiments, reports can include duty roster report(s), order tracker report(s), daily count report(s), daily order trend report(s), productivity report(s), accuracy report(s), re-work report(s), re-design report(s), turnaround time report(s), open ticket report(s), etc. to analyze and improve dental product design processes. In some embodiments, master data can include details of dental product(s), material(s) required to be used in a restoration, material and product mapping for auto selecting a product based on the material name requested for the restoration, price list(s) for billing customers based on different combinations of product, turn-around time etc., designation(s) that define a user's role, employee(s) that lists designer users, manufacturer(s) when fabrication of a dental product order is to be routed to an external partner (e.g., per instruction in the detail product order), customer(s) support type(s) that lists categories used to support customers (e.g., dental labs) to raise questions or ask for help, re-design categories (e.g., a list of conditions because of which a customer can request re-design of a dental product order) and code(s) (e.g., a codification system for subcategories under the list of re-design categories), quality control parameter(s) (e.g., a list of dental product design and manufacturing quality control parameters) and template(s) (e.g., a form based out of quality control parameters such that each parameter has a specific rating), customer preference, design code(s), etc. In some embodiments, user management can allow a user to handle management of the design center, customer(s), and manufacturer(s).

In an embodiment, the network 118 is representative of the Internet. In an embodiment, the network 40 can include one or more local area networks (LANs), one or more wide area networks (WANs), one or more wireless networks, one or more cellular data networks, suitable combinations thereof, or the like. In an embodiment, aspects of the network 118 can be the same as or similar to aspects of the network 540 as shown and described in accordance with FIG. 4 below.

FIG. 2 illustrates a flowchart of a method 200 for providing financial management and reconciliation within the dental project management system 200, according to one embodiment. The method 200 begins at 205 whereby a dental lab computer 110 uploads an invoice regarding a particular dental product project to the dental product management platform 120. In some embodiments, the invoice can be uploaded to the dental product management platform 120 upon fabrication of a dental product for a dental office. In some embodiments, the dental lab computer 110 can access and upload the invoice to the dental product management platform 120 via, for example, a GUI accessible via a website and/or online software application. When the dental product management platform 120 receives the invoice, the method 200 proceeds to 210.

At 210, the invoice is automatically validated by the dental product management platform 120. In some embodiments, the dental product management platform 120 can include an artificial intelligence (AI) validation module that is configured to validate invoices. The AI validation module can, for example, compare an invoice with established business rules (e.g., DSO specific doctor rates based on arrangement(s) between the DSO and the dental lab(s) review product material(s) (including, for example, brand preferences) selected in previous dental product cases by the doctor and auto select the same product material(s) for the same restoration type when not identified in the invoice; special discounts given to doctors for specific restoration types; shipping rules (e.g., overnight, batch delivery, specific delivery partner(s), specific delivery instruction(s), etc.); etc.) and previous user behavior (e.g., previous doctor preferences for product material and brand specifications for a particular combination of restoration and product type—in some instances the dental product prescription can have a generic value present and the doctor would communicate with the lab and get a waiver or discount on a particular type of dental product case; identifying mismatches in the dental order prescription from a work ticket sent by the doctor as doctors can sometimes mention a specific aspect in the dental product prescription (e.g., particular material type, brand preference, etc.) over other types of communication and instruct a dental lab on specific manufacturing conditions that may not be captured elsewhere but may have to be identified and captured during invoice reconciliation; etc.) based on AI training to validate the invoice. In some embodiments, the AI validation module can extract data points from the invoice and can identify and classify the extracted data points to determine, for example, the doctor, the DSO, established business rules, etc. In some embodiments, the AI validation module can compare the extracted data points with past validated invoices (e.g., for a particular doctor name, a prescribed product, a restoration type, dental lab being commissioned, etc.) and determine any deviation from a previous invoice. In some embodiments these factors can be retrieved from the dental product prescription and can be matched to existing conditions and changes made in the past to validate any new invoice. In some embodiments, invoices that match one or more pre-existing established rules can be deemed valid and any invoices with a deviation from the one or more pre-existing established rules can be flagged as ambiguous. Those invoices flagged as ambiguous may require manual intervention from which the AI validation module can learn from the manual intervention activity and build this into the training for the next time a similar invoice is reviewed. Upon completion of the validation, the method 200 proceeds to 215.

At 215, the dental product management platform 120 determines whether the invoice is validated based on the automatic validation performed at 210. In some embodiments, validation can be determined based on a Boolean scoring system between 0 and 1000 such that only those invoices scoring a 100 are validated. In other embodiments, the validation can be determined for those invoices scoring above a threshold number less than 100 but greater than 0. It will be appreciated that even if 10% of all invoices are automatically deemed validated at 215, the amount of manual effort required to validate all invoices can be greatly reduced. If the dental product management platform 120 determines that the invoice is validated, the method 200 proceeds to 230. If the dental product management platform 120 determines that the invoice is not valid or it is ambiguous whether the invoice is valid, the method 200 proceeds to 220.

At 220, the dental product management platform 120 communicates with the DSO computer 112 and requests a manual validation of the invoice. In some embodiments, a finance team of the DSO can perform the manual validation and then upload the manual validation result (e.g., invoice validated or invoice invalidated) via, for example, the DSO computer 112 using a GUI accessible via a website and/or online software application to the dental product management platform 120. The method 200 then proceeds to 225.

At 225, the dental product management platform 120 trains the AI validation module based on the manual validation result obtained at 220. For example, in some embodiments, extracted data points obtained at 210 can be reviewed manually and the resulting validation result can be captured by the AI validation module with the option to add new business rule(s) for use by the AI validation module for future invoices. If the new business rule(s) is selected, the new business rule(s) can be added to established business rules used by the AI validation module for future invoices. The method 200 then proceeds to 230.

At 230, the dental product management platform 120 communicates a validation feedback request to a doctor via, for example, a computer accessing a GUI of the dental product management platform 120. The validation feedback request can include a request for the doctor to validate the invoice and provide feedback on the quality of the dental lab's work after the invoice is automatically validated at 210. In some embodiments, the dental product management platform 120 can communicate the validation feedback request to the doctor via, for example, the intraoral scanner 205. Upon receipt of the validation feedback from the doctor, the method 200 proceeds to 235.

At 235, the dental product management platform 120 trains the AI validation module based on the validation feedback obtained at 230. In some embodiments, the AI validation module can capture feedback regarding the actual dental product delivered to the doctor and the dental product management platform 120 can request doctor sign-off of the invoice generated for each dental product case. If a doctor disagrees with an invoice sign-off, the invoice can be flagged to the DSO finance team in charge of the invoice manual intervention at 220. The DSO finance team can then analyze the invoice and the dental product prescription. If the invoice appears to be correct, the DSO finance team can contact the doctor to determine the doctor's issue with sign-off of the particular dental product case. If the DSO finance team determines that the doctor has a valid reason for not signing-off on the invoice, the DSO finance team can create a new business rule for use by the AI validation module to mitigate the issue for future invoices.

By using an AI validation module to automatically validate an invoice, the method 200 can decrease the amount of time required to validate and authorize a valid invoice and can learn from deviations from normal validation. Also, the method 200 can provide visibility from an initial patient visit through the dental product project creation. Also, the method 200 allows for the AI validation module of the dental product management platform 120 to be trained upon every invoice validation. Accordingly, the method 200 can assist a DSO in identifying and monitoring key focus areas such as, for example, doctor name, restoration detail(s), dental product order details(s), cost of dental product order component(s), business rules specific to a doctor or DSO, business rules specific to a restoration type, past deviations and accepted modifications to invoices for a particular doctor and/or DSO and/or restoration type, etc. Also, as the AI validation module is configured to extract data from a dental product prescription, an invoice, any worksheets, etc., the method 200 can also monitor aspects including: special instruction(s) from a doctor; product preferences of a doctor; manufacturing preferences of a doctor; manufacturing preferences for a particular restoration type; etc.

In particular, as all extracted data points are captured and monitored by the AI validation module, the DSO can utilize the extracted data points to derive insight as to what invoices should be validated. In some embodiments, the AI validation module can focus on extracted data points that can indicate, for example, a pricing mismatch or disparity, usage pattern of products for particular doctors, complicated dental product orders that can lead to special business rules for implementation by the AI validation module.

FIG. 3 illustrates a flowchart of a method 300 for providing interactive voice response (IVRS) within the dental project management platform 120 while a user is calling a support phone number of the dental product management system 120, according to one embodiment.

The method 300 begins at 310 whereby the support phone number of the dental product management platform 120 receives an incoming call from a dental office (e.g., a dental office including the dental lab computer 110).

At 320, an IVRS API of the dental product management platform 120 identifies the user (e.g., doctor/dental office) calling the support phone number at 310. In some embodiments, the IVRS API can check if the phone number calling the support phone number at 310 is associated with a registered doctor/dental office stored within a dental office database maintained by the dental product management platform 120 to identify the doctor/dental office calling the support phone number. When the IVRS API identifies the doctor/dental office, the method 300 proceeds to 330.

At 330, the IVRS API instructs a backend server of the dental product management platform 120 to load all dental product cases associated with the doctor/dental office identified at 320. In some embodiments, the backend server can access a dental product case database maintained by the dental product management platform 120. The method 330 then proceeds to 340.

At 340, the IVRS API provides the user with an option to specify one or more of a dental product case identification number, a patient identification number, a dental lab identification number that the user is trying to obtain additional details. The method 300 then proceeds to 350.

At 350, the IVRS API receives from the user identification details regarding a specific dental product case that the user is trying to obtain additional details. In some embodiments, the user can provide the identification details over the phone call by inputting numbers from the user's phone keypad, by speaking the identification details over the phone, etc. The method 300 then proceeds to 360.

At 360, the IVRS API uses the identification details received at 350 to retrieve, from the backend server, case specific details of a particular dental product case associated with the identification details. The method 300 then proceeds to 370.

At 370, the IVRS API provides case specific details for the particular dental product case retrieved at 360 to the user over the phone. The IVRS API can also provide additional support options to the user. In some embodiments, the case specific details can include for example a status of the dental product case, a dental lab working on the dental product case, shipment status, invoice details, billing status, etc. The method 300 can then proceed to optional 380.

At optional 380, the IVRS API receives from the user a request for additional support option. For example, the user can provide desired support details and request for a callback from the dental lab working on the dental product case. In some embodiments, the user can request a support ticket for a particular dental product case so that the phone call can be logged by the dental product management platform 120 for future reference. The method 300 then proceeds to optional 390.

At optional 390, the IVRS API can generate a support ticket for the particular dental product case and store the support ticket with the case specific details of the dental product case in the dental product case database. In some embodiments, the generated support ticket can include one or more action items for a support team of the dental product management platform 120 based on the desired support details provided by the user at 380.

Figure 4:
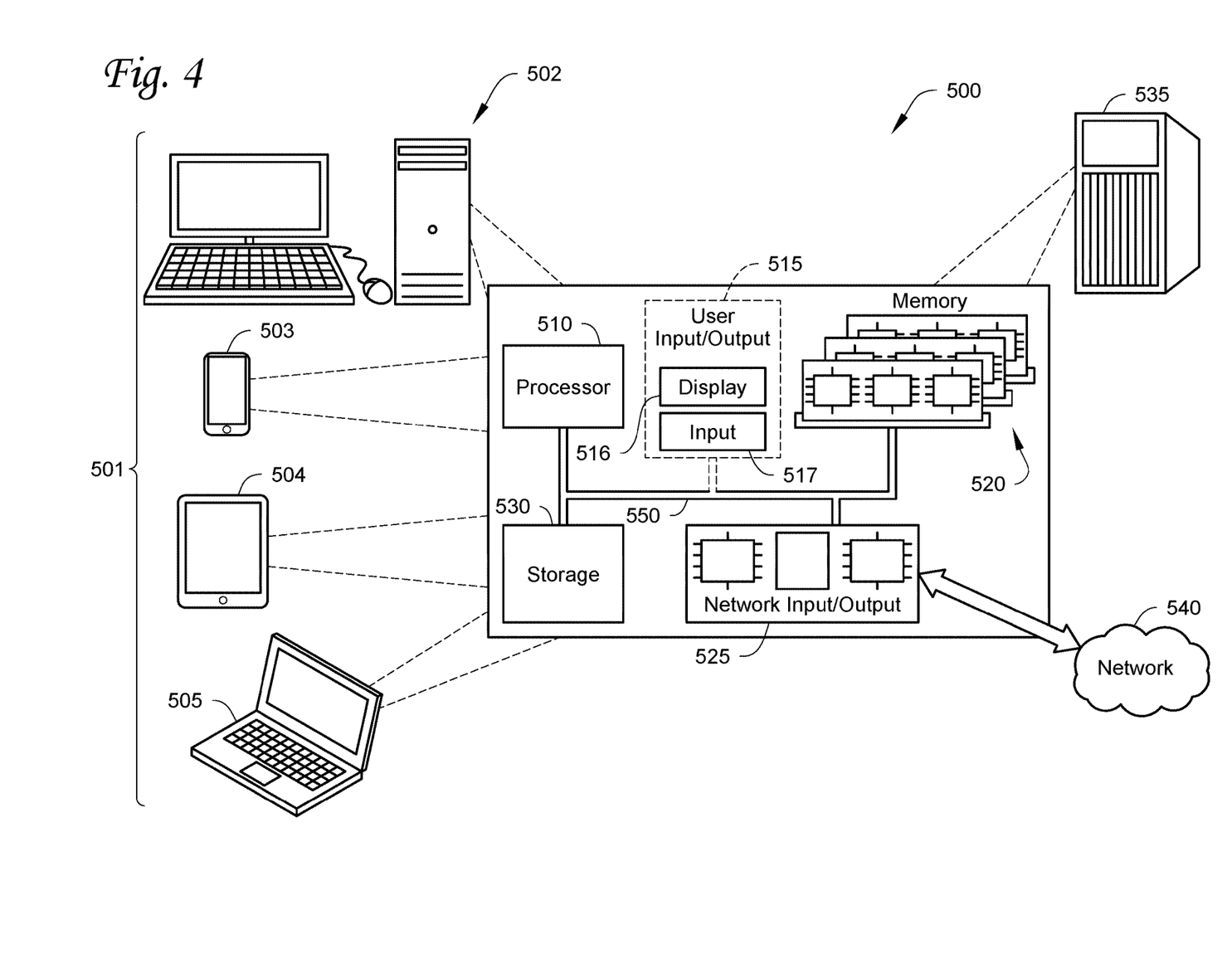
FIG. 4 is a schematic diagram of architecture for a computer device, according to one embodiment.

FIG. 4 is a schematic diagram of architecture for a computer device 500, according to an embodiment. The computer device 500 and any of the individual components thereof can be used for any of the operations described in accordance with any of the computer-implemented methods described herein.

The computer device 500 generally includes a processor 510, memory 520, a network input/output (I/O) 525, storage 530, and an interconnect 550. The computer device 500 can optionally include a user I/O 515, according to some embodiments. The computer device 500 can be in communication with one or more additional computer devices 500 through a network 540.

The computer device 500 is generally representative of hardware aspects of a variety of user devices 501 and a server device 535. The illustrated user devices 501 are examples and are not intended to be limiting. Examples of the user devices 501 include, but are not limited to, a desktop computer 502, a cellular/mobile phone 503, a tablet device 504, and a laptop computer 505. It is to be appreciated that the user devices 501 can include other devices such as, but not limited to, a wearable device, a personal digital assistant (PDA), a video game console, a television, or the like. In an embodiment, the user devices 501 can alternatively be referred to as client devices 501. In such an embodiment, the client devices 501 can be in communication with the server device 535 through the network 540. One or more of the client devices 501 can be in communication with another of the client devices 501 through the network 540 in an embodiment.

The processor 510 can retrieve and execute programming instructions stored in the memory 520 and/or the storage 530. The processor 510 can also store and retrieve application data residing in the memory 520. The interconnect 550 is used to transmit programming instructions and/or application data between the processor 510, the user I/O 515, the memory 520, the storage 530, and the network I/O 540. The interconnect 550 can be, for example, one or more busses or the like. The processor 510 can be a single processor, multiple processors, or a single processor having multiple processing cores. In some embodiments, the processor 510 can be a single-threaded processor. In an embodiment, the processor 510 can be a multi-threaded processor.

The user I/O 515 can include a display 516 and/or an input 517, according to an embodiment. It is to be appreciated that the user I/O 515 can be one or more devices connected in communication with the computer device 500 that are physically separate from the computer device 500. For example, the display 516 and input 517 for the desktop computer 502 can be connected in communication but be physically separate from the computer device 500. In some embodiments, the display 516 and input 517 can be physically included with the computer device 500 for the desktop computer 502. In an embodiment, the user I/O 515 can physically be part of the user device 501. For example, the cellular/mobile phone 503, the tablet device 504, and the laptop 505 include the display 516 and input 517 that are part of the computer device 500. The server device 535 generally may not include the user I/O 515. In an embodiment, the server device 535 can be connected to the display 516 and input 517.

The display 516 can include any of a variety of display devices suitable for displaying information to the user. Examples of devices suitable for the display 516 include, but are not limited to, a cathode ray tube (CRT) monitor, a liquid crystal display (LCD) monitor, a light emitting diode (LED) monitor, or the like.

The input 517 can include any of a variety of input devices or input means suitable for receiving an input from the user. Examples of devices suitable for the input 517 include, but are not limited to, a touchscreen, a keyboard, a mouse, a trackball, a button, a voice command, a proximity sensor, an ocular sensing device for determining an input based on eye movements (e.g., scrolling based on an eye movement), or the like. It is to be appreciated that combinations of the foregoing inputs 517 can be included for the user devices 501. In some embodiments the input 517 can be integrated with the display 516 such that both input and output are performed by the display 516.

The memory 520 is generally included to be representative of a random access memory such as, but not limited to, Static Random Access Memory (SRAM), Dynamic Random Access Memory (DRAM), or Flash. In some embodiments, the memory 520 can be a volatile memory. In some embodiments, the memory 520 can be a non-volatile memory. In some embodiments, at least a portion of the memory can be virtual memory.

The storage 530 is generally included to be representative of a non-volatile memory such as, but not limited to, a hard disk drive, a solid state device, removable memory cards, optical storage, flash memory devices, network attached storage (NAS), or connections to storage area network (SAN) devices, or other similar devices that may store non-volatile data. In some embodiments, the storage 530 is a computer readable medium. In some embodiments, the storage 530 can include storage that is external to the computer device 500, such as in a cloud.

The network I/O 525 is configured to transmit data via a network 540. The network 540 may alternatively be referred to as the communications network 540. Examples of the network 540 include, but are not limited to, a local area network (LAN), a wide area network (WAN), the Internet, or the like. In some embodiments, the network I/O 525 can transmit data via the network 540 through a wireless connection using Wi-Fi, Bluetooth, or other similar wireless communication protocols. In some embodiments, the computer device 500 can transmit data via the network 540 through a cellular, 3G, 4G, or other wireless protocol. In some embodiments, the network I/O 525 can transmit data via a wire line, an optical fiber cable, or the like. It is to be appreciated that the network I/O 525 can communicate through the network 540 through suitable combinations of the preceding wired and wireless communication methods.

The server device 535 is generally representative of a computer device 500 that can, for example, respond to requests received via the network 540 to provide, for example, data for rendering an online service (e.g., a website, an app, etc.) on the user devices 501. The server 535 can be representative of a data server, an application server, an Internet server, or the like.

Aspects described herein can be embodied as a system, method, or a computer readable medium. In some embodiments, the aspects described can be implemented in hardware, software (including firmware or the like), or combinations thereof. Some aspects can be implemented in a non-transitory, tangible computer readable medium, including computer readable instructions for execution by a processor. Any combination of one or more computer readable medium(s) can be used.

The computer readable medium can include a computer readable signal medium and/or a computer readable storage medium. A computer readable storage medium can include any tangible medium capable of storing a computer program for use by a programmable processor to perform functions described herein by operating on input data and generating an output. A computer program is a set of instructions that can be used, directly or indirectly, in a computer system to perform a certain function or determine a certain result. Examples of computer readable storage media include, but are not limited to, a floppy disk; a hard disk; a random access memory (RAM); a read-only memory (ROM); a semiconductor memory device such as, but not limited to, an erasable programmable read-only memory (EPROM), an electrically erasable programmable read-only memory (EEPROM), Flash memory, or the like; a portable compact disk read-only memory (CD-ROM); an optical storage device; a magnetic storage device; other similar device; or suitable combinations of the foregoing. A computer readable signal medium can include a propagated data signal having computer readable instructions. Examples of propagated signals include, but are not limited to, an optical propagated signal, an electro-magnetic propagated signal, or the like. A computer readable signal medium can include any computer readable medium that is not a computer readable storage medium that can propagate a computer program for use by a programmable processor to perform functions described herein by operating on input data and generating an output.

An embodiment can be provided to an end-user through a cloud-computing infrastructure. Cloud computing generally includes the provision of scalable computing resources as a service over a network (e.g., the Internet or the like).

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

What is claimed is:

1. A method for providing financial management and reconciliation within a dental product management system, the method comprising:
the dental project management system, supported by a processor and memory, receiving an invoice associated with a particular dental product project;
an artificial intelligence (AI) validation module of the dental product management system automatically validating the invoice;
upon validation of the invoice, the dental product management system requesting feedback from a doctor at a dental office;
the dental product management system receiving feedback from the doctor; and
training the AI validation module based on the feedback from the doctor.

2. The method of claim 1, further comprising the AI validation module requesting manual validation of the invoice upon the AI validation module being unable to validate the invoice.

3. The method of claim 2, further comprising training the AI validation module based on a result of the manual validation of the invoice.

4. The method of claim 1, wherein a graphical user interface (GUI) of the dental product management system receiving the invoice from a dental lab computer.

5. The method of claim 1, wherein the dental project management system receives the invoice upon fabrication of a dental product based on the particular dental product project.

6. The method of claim 1, wherein the AI validation module automatically validating the invoice by comparing the invoice with one or more established business rules.

7. The method of claim 6, wherein the established business rules include at least one of: a DSO specific doctor rate; a special discount provided for a specific restoration type; shipping rules; and previous user behavior; and identifying a mismatch in a dental order prescription from a work ticket sent by the doctor.

8. The method of claim 1, wherein the AI validation module automatically validating the invoice includes the AI validation module:
   extracting one or more data points from the invoice;
   identifying and classifying the one or more data points to determine at least one of the doctor, a dental service organization, and one or more established business rules.

9. A dental product management system configured to provide financial management and reconciliation within a dental product management system, the dental product management system comprising:
   a processor and a memory configured to support the dental product management system; and
   an artificial intelligence (AI) validation module configured to automatically validate an invoice associated with a particular dental product project;
   wherein the dental project management system is configured to receive the invoice,
   wherein upon validation of the invoice, the dental product management system is configured to request feedback from a doctor at a dental office,
   wherein the dental product management system is configured to receive feedback from the doctor, and
   wherein the dental product management system is configured to train the AI validation module based on the feedback from the doctor.

10. The dental product management system of claim 9, wherein the AI validation module is configured to request manual validation of the invoice upon the AI validation module being unable to validate the invoice.

11. The dental product management system of claim 10, wherein the dental product management system is configured to train the AI validation module based on a result of the manual validation of the invoice.

12. The dental product management system of claim 9, further comprising a graphical user interface (GUI) configured to receive the invoice from a dental lab computer.

13. The dental product management system of claim 9, wherein the dental project management system is configured to receive the invoice upon fabrication of a dental product based on the particular dental product project.

14. The dental product management system of claim 9, wherein the AI validation module is configured to automatically validate the invoice by comparing the invoice with one or more established business rules.

15. The dental product management system of claim 14, wherein the established business rules include at least one of: a DSO specific doctor rate; a special discount provided for a specific restoration type; shipping rules; and previous user behavior; and identifying a mismatch in a dental order prescription from a work ticket sent by the doctor.

16. The dental product management system of claim 9, wherein the AI validation module is configured to automatically validate the invoice includes the AI validation module being configured to:
   extract one or more data points from the invoice;
   identify and classifying the one or more data points to determine at least one of the doctor, a dental service organization, and one or more established business rules.

* * * * *